United States Patent
Boucher, Jr.

(10) Patent No.: US 6,264,975 B1
(45) Date of Patent: Jul. 24, 2001

(54) METHODS OF HYDRATING MUCOSAL SURFACES

(75) Inventor: Richard C. Boucher, Jr., Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/421,705

(22) Filed: Oct. 20, 1999

Related U.S. Application Data

(60) Provisional application No. 60/104,999, filed on Oct. 20, 1998.

(51) Int. Cl.$^7$ .......................... A61F 13/00; A01N 43/60; A61K 31/495

(52) U.S. Cl. .......................... 424/434; 514/255

(58) Field of Search .............................. 424/434; 514/255

(56) References Cited

U.S. PATENT DOCUMENTS

| | | | |
|---|---|---|---|
| 3,313,813 | 4/1967 | Cragoe, Jr. | 260/250 |
| 4,294,829 | 10/1981 | Suzuki et al. | 424/241 |
| 4,389,393 | 6/1983 | Schor et al. | 424/19 |
| 4,835,142 | 5/1989 | Suzuki et al. | 514/53 |
| 4,894,376 | 1/1990 | Morad et al. | 514/255 |
| 5,635,160 | 6/1997 | Stutts, III et al. | 424/45 |
| 5,656,256 * | 8/1997 | Boucher et al. | 424/45 |
| 5,707,644 | 1/1998 | Illum | 424/434 |
| 5,789,391 | 8/1998 | Jacobus et al. | 514/51 |
| 5,876,700 * | 3/1999 | Boucher, Jr. | 424/45 |

OTHER PUBLICATIONS

Knowles et al Activation by extracellular nucleotides of chloride secretion in the airway epithelia of patients with cystic fibrosis. The New England Journal of Medicine 325(8):533–538 (1991).*

Benos et al., Purification and characterization of the amiloride–sensitive sodium channel from A6 cultured cells and bovine renal papilla, *Proc. Natl. Acad. Sci. USA*, 83:8525–8529 (1986).

Kleyman et al., New amiloride analogue as hapten to raise anti–amiloride antibodies, *Am. J. Physiol*, 250 (Cell Physiol. 19):C165–C170 (1986).

Kleyman et al., Amiloride and Its Analogs as Tools in the Study of Ion Transport, *J. Membrane Biol.*, 105:1–21 (1988).

* cited by examiner

Primary Examiner—Thurman K. Page
Assistant Examiner—Todd D Ware
(74) *Attorney, Agent, or Firm*—Myers Bigel Sibley & Sajovec

(57) ABSTRACT

A method of hydrating nasal airway surfaces in a subject in need of such treatment comprises topically applying a sodium channel blocker to a nasal airway surface of the subject in an amount effective to inhibit the reabsorption of water by the surface. The channel blocker may be a pyrazinoylguanidine sodium channel blocker, such as benzamil, phenamil, amiloride, or a pharmaceutically acceptable salts thereof. The method may further comprise the step of topically applying a $P2Y_2$ receptor agonist to a nasal airway surface of the subject in an amount effective to stimulate chloride secretion by the nasal airway surface. In a preferred embodiment, the sodium channel blocker is a covalent conjugate of a pyrazinoylguanidine sodium channel blocker and a non-absorbable carrier moiety (e.g., albumin, polyethylene glycol). Such compounds may also be administered to other mucosal surfaces where it is desired to inhibit the reabsorption of water.

43 Claims, No Drawings

METHODS OF HYDRATING MUCOSAL SURFACES

RELATED APPLICATIONS

This application claims priority from provisional application Ser. No. 60/104,999, filed Oct. 20, 1998, the disclosure of which is incorporated by reference herein in its entirety.

This invention was made with government support under grant number 2 P01 HL34322 from the National Institutes of Health. The United States government has certain rights to this invention.

FIELD OF THE INVENTION

The present invention concerns methods of hydrating nasal airway surfaces in patients in need of such treatment, along with compounds and compositions usefull for carrying out such methods.

BACKGROUND OF THE INVENTION

The current therapy for hydrating nasal airway surfaces is to apply normal saline via drops or spray delivery devices. The disadvantage of this simple approach is that the duration of effect is short. It would be desireable to provide a way to achieve a more lasting hydration of nasal airway surfaces.

U.S. Pat. No. 5,789,391 to Jacobus describes methods of treating sinusitis with uridine triphosphates and related compounds such as UTP or $P^1,P^4$-di(uridine-5' tetraphosphate ($U_2P_4$) in an amount effective to promote drainage of congested fluid in the sinuses by hydrating mucous secretions or by stimulating ciliary beat frequency in the sinuses.

U.S. Pat. No. 4,501,729 to Boucher describes the use of respirable or non-respirable amiloride to hydrate airway mucous secretions, and U.S. Pat. No. 5,656,256 to Boucher and Stutts describes the use of respirable or non-respirable benzamil and phenamil to hydrate lung mucous secretions. The use of amiloride, benzamil or phenamil to hydrate nasal airway surfaces is neither disclosed nor suggested.

SUMMARY OF THE INVENTION

A first aspect of the present invention is a method of hydrating nasal airway surfaces in a subject in need of such treatment. The method comprises topically applying a sodium channel blocker to a nasal airway surface of the subject in an amount effective to inhibit the reabsorption of water by the nasal airway surface. The channel blocker may be a pyrazinoylguanidine sodium channel blocker, such as benzamil, phenamil, amiloride, or a pharmaceutically acceptable salt thereof.

The method may further comprise the step of topically applying a $P2Y_2$ receptor agonist to a nasal airway surface of the subject in an amount effective to stimulate chloride secretion, and thereby stimulate water secretion, by the nasal airway surface.

A second aspect of the present invention is a method of hydrating mucosal surfaces such as airway surfaces in a subject in need of such treatment, comprising topically applying a sodium channel blocker to a mucosal surface such as an airway surface of the subject in an amount effective to inhibit the reabsorption of water by the surface, wherein the sodium channel blocker is a covalent conjugate of a pyrazinoylguanidine sodium channel blocker and a non-absorbable carrier moiety (e.g., polyethylene glycol, albumin; carbohydrate).

Again, the method may further comprise the step of topically applying a $P2Y_2$ receptor agonist to a mucosal surface such as an airway surface of the subject in an amount effective to stimulate chloride secretion by the surface.

A third aspect of the present invention is a pharmaceutical formulation, comprising a sodium channel blocker in a pharmaceutically acceptable carrier (e.g., an aqueous carrier solution); wherein the sodium channel blocker is a covalent conjugate of a pyrazinoylguanidine sodium channel blocker and a non-absorbable carrier moiety; preferably subject to the proviso that the non-absorbable carrier moiety is not bovine serum albumin or rabbit serum albumin. The composition may further contain a $P2Y_2$ receptor agonist.

A fourth aspect of the present invention is a compound useful as a sodium channel blocker, the compound comprising a covalent conjugate of a pyrazinoylguanidine sodium channel blocker and a non-absorbable carrier moiety; preferably subject to the proviso that the non-absorbable carrier moiety is not bovine serum albumin, rabbit serum albumin or agarose. For example, the carrier moiety can be polyethylene glycol or human serum albumin, or a carbohydrate.

A fifth aspect of the present invention is the use of compounds as described above for the preparation of a medicament for the treatment of disorders as described herein.

The present invention is explained in greater detail in the specification below.

DETAILED DESCRIPTION OF PREFERRED EMBODIMENTS

The term "airway surface" as used refers to airway surfaces below the larynx and in the lungs, as well as air passages in the head, including the sinuses, in the region above the larynx.

The term "nasal airway surface" as used herein refers to the airways and associated air passages in the head, including the sinuses, in the region above the larynx. This definition excludes airways below the larynx, which have been the target of drug delivery for different purposes.

The term alkyl or loweralkyl as used herein refers to C1 to C4 alkyl, which may be linear or branched and saturated or unsaturated. Cycloalkyl is specified as such herein, and is typically C3, C4 or C5 to C6 or C8 cycloalkyl. Alkenyl or loweralkenyl as used herein likewise refers to C1 to C4 alkenyl, and alkoxy or loweralkoxy as used herein likewise refers to C1 to C4 alkoxy. Halo as used herein refers to any halogen, such as chloro, fluoro, bromo, or iodo.

The term "non-absorbable carrier moiety" as used herein refers to a functional group that serves to trap the compound containing the group on airway surfaces, or adhere the compound to airway surfaces, and partly or wholly inhibits the absorption of the compound by the surface on which it is deposited.

Subjects that may be treated by the methods of the present invention include patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient.

Subjects that may be treated by the method of the present invention also include patients being nasally administered supplemental oxygen (which tends to dry the airway surfaces), patients afflicted with an allergic disease or response (e.g., an allergic response to pollen, dust, animal hair or particles, insects or insect particles, etc.) that affects nasal airway surfaces, patients afflicted with a bacterial infection (e.g., staphylococcus infections such as staphylococcus aureus infections, Hemophilus influenza infections, streptococcus pneumoniae infections, pseudomonas infections, etc.) of the nasal airway surfaces, an inflammatory disease that affects nasal airway surfaces, or patients afflicted with sinusitis (wherein the active agent or agents are administered to promote drainage of congested mucous secretions in the sinuses by administering an amount effective to promote drainage of congested fluid in the sinuses).

The present invention may be used to hydrate mucosal surfaces other than airway surfaces. Such other mucosal surfaces include gastrointestinal surfaces, oral surfaces, genito-ureteral surfaces, ocular surfaces or surfaces of the eye, the inner ear, and the middle ear. For example, the active compounds of the present invention may be administered by any suitable means, including orally or rectally, in an amount effective to combat constipation in a subject.

The present invention is concerned primarily with the treatment of human subjects, but may also be employed for the treatment of other mammalian subjects, such as dogs and cats, for veterinary purposes.

1. Active Agents.

Pyrazinoylguanidine sodium channel blockers are disclosed in U.S. Pat. No. 3,313,813 to Cragoe. (Applicant specifically intends that the disclosure of this and all other U.S. Patent references cited herein be incorporated by reference herein in their entirety).

Amiloride, one particular pyrazinoylguanidine sodium channel blocker, is described at Merck Index Registry No. 426 (12$^{th}$ Ed. 1996).

Benzamil (also known as 3,5-diamino-6-chloro-N-(benzylaminoaminomethylene) pyrazinecarboxamide) and phenamil (also known as 3,5-diamino-6-chloro-N-(phenylaminoaminomethylene)pyrazinecarboxamide) are known compounds and are disclosed in U.S. Pat. No. 3,313,813 to E. Cragoe (applicant specifically intends that the disclosure of this and all other patents cited herein be incorporated herein by reference).

Various additional pyrazinoylguanidine sodium channel blockers that are amiloride analogs are disclosed and described in T. Kleyman and E. Cragoe, Amiloride and its Analogs as Tools in the Study of ion Transport, *J. Membrane Biol.* 105, 1–21 (1988).

Specific examples of active compounds that may be used to carry out the present invention are the pyrazinoylguanidine sodium channel blockers disclosed in U.S. Pat. No. 3,313,813, incorporated by reference above. Such compounds have the formula:

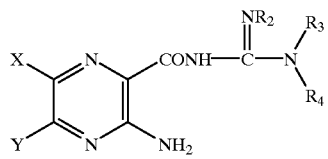

wherein:
X is selected from the group consisting of chloro, bromo, iodo, loweralkyl, lower-cycloalkyl having from 3 to 7 carbons, phenyl, chlorophenyl, bromophenyl, X'-thio and X'-sulfonyl wherein X' is selected from the group consisting of loweralkyl and phenyl-loweralkyl. Preferably, X is chloro.

Y is selected from the group consisting of hydroxyl, mercapto, loweralkyloxy, loweralkylthio, chloro, loweralkyl, lowercycloalkyl having from 3 to 6 carbons, phenyl, amino having the structure:

wherein:
R is selected from the group consisting of hydrogen, amino, amidino, lower-cycloalkyl having 3 to 6 carbon atoms, loweralkyl, hydroxyloweralkyl, haloloweralkyl, lower-(cycloalkylalkyl) having 3 to 6 carbons in the ring, phenyl-loweralkyl, lower-(alkylaminoalkyl), lower-alkenyl, phenyl, halophenyl, and lower-alkylphenyl. In one preferred embodiment, Y is chloro; in another preferred embodiment, Y is amino.

$R_1$ is selected from the group consisting of hydrogen, loweralkyl, loweralkenyl, and additionally;

R and $R_1$ can be joined to form a lower alkylene.

$R_2$ is selected from the group consisting of hydrogen and loweralkyl.

Preferably, R, $R_1$, and $R_2$ are hydrogen.

$R_3$ and $R_4$ respectively are independently selected from the group consisting of hydrogen, loweralkyl, hydroxyloweralkyl, phenyl-loweralkyl, (halophenyl)-loweralkyl, lower-(alkylphenylalkyl), (loweralkoxyphenyl)-loweralkyl, naphthyl-loweralkyl, (octahydro-1-azocinyl)-loweralkyl, pyridyl-loweralkyl, and loweralkyl radicals linked to produce with the nitrogen atom to which they are attached a 1-pyrrolidinyl, piperidino, morpholino, and a 4-loweralkyl-piperazinyl group, and phenyl. Preferably, $R_3$ is hydrogen, phenyl, or phenylalkyl. Preferably, $R_4$ is hydrogen.

2. Pharmaceutically Acceptable Salts

The term "active agent" as used herein, includes the pharmaceutically acceptable salts of the compound, such as (but not limited to) benzamil hydrochloride or phenamil hydrochloride. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agent used to prepare compositions for the present invention may alternatively be in the form of a pharmaceutically acceptable free base of active agent. Because the free base of the compound is less soluble than the salt, free base compositions are employed to provide more sustained release of active agent to the lungs. Active agent present in the lungs in particulate form which has not gone into solution is not available to induce a physiological response, but serves as a depot of bioavailable drug which gradually goes into solution.

3. Formulations and Administration

A third aspect of the present invention is a pharmaceutical formulation, comprising a sodium channel blocker in a pharmaceutically acceptable carrier (e.g., an aqueous carrier solution); wherein the sodium channel blocker is a covalent conjugate of a pyrazinoylguanidine sodium channel blocker and a non-absorbable carrier moiety; preferably subject to the proviso that the non-absorbable carrier moiety is not bovine serum albumin or rabbit serum albumin. In general, the sodium channel blocker is included in the composition in an amount effective to inhibit the reabsorption of water by airway surfaces, particularly nasal airway surfaces. As discussed below, the composition may further comprise a $P2Y_2$ receptor agonist or a pharmaceutically acceptable salt thereof (also sometimes referred to as an "active agent" herein). The $P2Y_2$ receptor agonist is typically included in an amount effective to stimulate chloride and water secretion by airway surfaces, particularly nasal airway surfaces.

The active compounds disclosed herein may be administered to the nasal airway surfaces of a patient by any suitable means, including as a spray, mist, or droplets of the active compounds in a pharmaceutically acceptable carrier such as physiological saline solution or distilled water. For example, the active compounds may be prepared as formulations and administered as described in U.S. Pat. No. 5,789,391 to Jacobus, the disclosure of which is incorporated by reference herein in its entirety.

In one preferred embodiment they are administered by administering an aerosol suspension of respirable or non-respirable particles (preferably non-respirable particles) comprised of the active compound, which the subject inhales through the nose. The respirable or non-respirable particles may be liquid or solid. The quantity of active agent included may be an amount sufficient to achieve dissolved concentrations of active agent on the nasal airway surfaces of the subject of from about $10^{-7}$ to about $10^{-3}$ Moles/liter, and more preferably from about $10^{-6}$ to about $10^{-4}$ Moles/liter.

In one embodiment of the invention, the particulate active agent composition may contain both a free base of active agent and a pharmaceutically acceptable salt such as benzamil hydrochloride or phenamil hydrochloride to provide both early release of and sustained release of active agent for dissolution into the mucous secretions of the nose. Such a composition serves to provide both early relief to the patient, and sustained relief over time. Sustained relief, by decreasing the number of daily administrations required, is expected to increase patient compliance with a course of active agent treatments.

Solid or liquid particulate active agent prepared for practicing the present invention should as noted above include particles of respirable or non-respirable size: that is, for respirable particles, particles of a size sufficiently small to pass through the mouth and larynx upon inhalation and into the bronchi and alveoli of the lungs, and for nonrespirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10–500 $\mu$m may be used to ensure retention in the nasal cavity.

The dosage of active compound will vary depending on the condition being treated and the state of the subject, but generally may be an amount sufficient to achieve dissolved concentrations of active compound on the nasal airway surfaces of the subject of from about $10^{-9}$ to about $10^{-3}$ Moles/liter, and more preferably from about $10^{-6}$ to about $3\times10^{-4}$ Moles/liter. Depending upon the solubility of the particular formulation of active compound administered, the daily dose may be divided among one or several unit dose administrations. The daily dose by weight may range from about 0.1, 0.5 or 1 to 10 or 20 milligrams of active agent particles for a human subject, depending upon the age and condition of the subject. A currently preferred unit dose is about 0.5, 1 or 2 milligrams of active agent given at a regimen of four administrations per day. The dosage may be provided as a prepackaged unit by any suitable means (e.g., encapsulating in a gelatin capsule).

Pharmaceutical formulations suitable for nasal administration include formulations of solutions, emulsions, suspensions and extracts. See generally, J. Nairn, Solutions, Emulsions, Suspensions and Extracts, in Remington: *The Science and Practice of Pharmacy*, chap. 86 (19$^{th}$ ed 1995). Pharmaceutical formulations suitable for nasal administration may be prepared as described in U.S. Pat. Nos. 4,389,393 to Schor; 5,707,644 to Illum; U.S. Pat. No. 4,294,829 to Suzuki; and U.S. Pat. No. 4,835,142 to Suzuki; the disclosures of which are incorporated by reference herein in their entirety.

In the manufacture of a formulation according to the invention, active agents or the physiologically acceptable salts or free bases thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a capsule, which may contain from 0.5% to 99% by weight of the active compound. One or more active compounds may be incorporated in the formulations of the invention, which formulations may be prepared by any of the well-known techniques of pharmacy consisting essentially of admixing the components.

Mists or aerosols of liquid particles comprising the active compound may be produced by any suitable means, such as by a simple nasal spray with the active agent in an aqueous pharmaceutically acceptable carrier, such as sterile saline solution or sterile water. Administration may be with a pressure-driven aerosol nebulizer or an ultrasonic nebulizer. See, e.g., U.S. Pat. No. 4,501,729 and U.S. Pat. No. 5,656,256. Suitable formulations for use in a nasal droplet or spray bottle or in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Mists or aerosols of solid particles comprising the active compound may likewise be produced with any solid particulate medicament aerosol generator. Aerosol generators for administering solid particulate medicaments to a subject produce particles which are respirable or non-respirable, as explained above, and generate a volume of mist or aerosol containing a predetermined metered dose of a medicament at a rate suitable for human administration. One illustrative type of solid particulate aerosol generator is an insufflator. Suitable formulations for administration by insufflation include fmely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 $\mu$l to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants (such as oleic acid or sorbitan trioleate), antioxidants and suitable flavoring agents.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formation of an aerosol. A suitable dispersant is lactose, which may be blended with the active agent in any suitable ratio (e.g., a 1 to 1 ratio by weight).

4. Covalent Conjugates

As noted above, also disclosed is a method of hydrating nasal airway surfaces in a subject in need of such treatment, comprising topically applying a sodium channel blocker to a nasal airway surface of the subject in an amount effective to inhibit the reabsorption of water by the nasal airway surface, wherein the sodium channel blocker is a covalent conjugate of a pyrazinoylguanidine sodium channel blocker and a non-absorbable carrier moiety. The non-absorbable carrier moiety may be a carbohydrate, protein, peptide, amino acid, polyamine, or water soluble linear polymer, which may be directly linked to the sodium channel blocker or linked through an intermediate linking group such as an alkylene group. Other suitable carrier moieties include erythritol and xylotol.

Water soluble linear polymers useful as carrier moieties include polyvinylpyrrolidone, polyethylene glycol, nonylphenol ethoxylates, and polyvinyl alcohol.

Carbohydrates useful as carrier moieties include sugars and polysaccharides (including charged and uncharged polysaccharides), such as dextran, lactose, sialic acid and mannitol. An additional example is agarose.

Proteins or peptides useful as carrier moieties include albumin (for example, human serum albumin) and protamine.

Amino acids useful for carrying out the present invention include all twenty standard amino acids (alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, and histidine), in either the D or L configuration.

Polyamines useful for carrying out the present invention include spermine and spermidine.

In one embodiment, the conjugate has the formula:

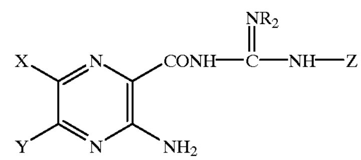

wherein:

X, Y, and $R_2$ are as described above, and Z is the non-absorbable carrier moiety covalently linked, directly or indirectly, to the adjacent nitrogen atom.

An of a variety of approaches for linking the pyrazinoylguanidine sodium channel blocker to the non-absorbable moiety may be employed, as discussed below.

A direct linkage by a caproate linker may be employed by reacting the nonabsorbable moiety with intermediates as follows, in accordance with known techniques:

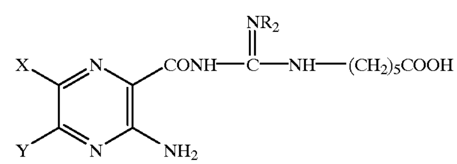

where X, Y, and $R_2$ are as given above.

Spacer linkers may be employed with intermediates as follows:

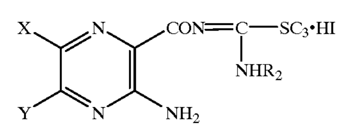

(T. Kleyman and E. Cragoe, *J. Membrane Biol.* 105, 1 (1988)(FIG. 2) where X, Y, and $R_2$ are as given above.

General linkers may be employed with intermediates as follows:

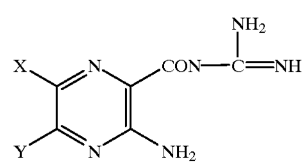

where X and Y are as described above.

Techniques for forming conjugates are known. A covalent conjugate of amiloride and bovine or rabbit serum albumin for use in creating anti-amiloride antibodies is disclosed in T. Kleyman et al., New Amiloride Analogue as Hapten to Raise Anti-Amiloride Antibodies, Am. *J. Physiol.* 250, C165–C170 (1986). This same technique can be performed with other amiloride analogs, and with other proteins or peptides. Thus, for example, a covalent conjugate of amiloride and analogs thereof, such as benzamil or phenamil, with human serum albumin can be produced in like manner.

Covalent conjugates of amiloride and SEPHAROSE™ brand agarose (a polysaccharide) are described in T. Kleyman et al., supra, and in D. Benos et al., *Proc. Natl. Acad. Sci. USA* 83, 8525–8529 (1986). Different brands, forms, and molecular weights of agarose may be employed, or other polysaccharides employed, or different amiloride analogs such as benzamil or phenamil may be employed, to make additional covalent conjugates by similar techniques.

5. P2Y₂ Receptor Agonists

The methods described above may further comprise the step of topically applying a $P2Y_2$ receptor agonist to a nasal airway surface of the subject in an amount effective to stimulate chloride secretion by the nasal airway surface. The concurrent topical application may be carried out by combining the P2Y2 receptor agonists with the active agent described above in a common pharmaceutically acceptable carrier solution. The agonist may be UTP or an analog thereof, as described in U.S. Pat. Nos. 5,789,391; 5,656,256 or 5,292,498, the disclosures of which are to be incorporated by reference herein in their entirety. Particularl preferred agonists are UTP, the UTP analog uridine 5'-O-(3-thiotriphosphate) (or "UTP gamma S"), or the UTP analog $P^1,P^4$-di (uridine-5') tetraphosphate (or "$U_2P_4$").

Concurrent application refers to essentially co-extensive application, or application to the same portion or portions of the nasal airway surfaces. Such concurrent or co-extensive application can be achieved by simultaneous administration, or by administration sufficiently close in time so that a the two agents achieve their therapeutic effect concurrently.

Additional examples of receptor agonists that can be used to carry out the present invention include those having the general formula:

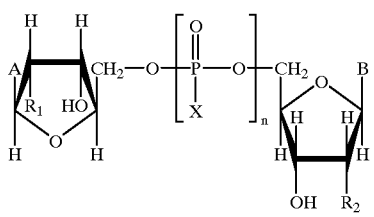

wherein:

A and B are each independently a purine or pyrimidine base (e.g., adenine, guanine, thymine, cytosine, uracil); preferably, A is uracil and B is cytosine;

$R_1$ and $R_2$ are each independently selected from the group consisting of H or OH; and n is from 1 to 5 or 6, preferably 2, 3 or 4.

The receptor agonists may be combined in the same formulation and administered in like manner as the active compounds described above, or as described in U.S. Pat. No. 5,656,256 or U.S. Pat. No. 5,292,498, the disclosures of which are to be incorporated by reference herein in their entirety.

The foregoing is illustrative of the present invention, and is not to be construed as limiting thereof. The invention is defined by the following claims, with equivalents of the claims to be included therein.

What is claimed is:

1. A method of hydrating a mucosal surface in a subject in need of such treatment, comprising:

topically applying a sodium channel blocker to a nasal airway surface of said subject in an amount effective to inhibit the reabsorption of water by said mucosal surface, wherein said sodium channel blocker is a covalent conjugate of a pyrazinoylguanidine sodium channel blocker and a non-absorbable carrier moiety.

2. A method according to claim 1, wherein said mucosal surface is a nasal airway surface and said patient is receiving nasal oxygen supplementation.

3. A method according to claim 1, wherein said mucosal surface is a nasal airway surface and said patient is afflicted with an allergic disorder affecting nasal airway surfaces.

4. A method according to claim 1, wherein said mucosal surface is a nasal airway surface and said patient is afflicted with an inflammatory disorder affecting nasal airway surfaces or a bacterial infection of the nasal airway surfaces.

5. A method according to claim 1, wherein said non-absorbable carrier moiety is selected from the group consisting of carbohydrates, proteins, peptides, polyamines, and water soluble linear polymers.

6. A method according to claim 5, wherein said non-absorbable carrier moiety is a water soluble linear polymer selected from the group consisting of polyvinylpyrrolidone, poyethylene glycol, nonylphenol ethoxylates, polyvinyl alcohol.

7. A method according to claim 5, wherein said non-absorbable carrier moiety is a carbohydrate selected from the group consisting of sugars and polysaccharides.

8. A method according to claim 5, wherein said non-absorbable carrier moiety is a carbohydrate selected from the group consisting of dextran, lactose, sialic acid, and mannitol.

9. A method according to claim 5, wherein said non-absorbable carrier moiety is a protein or peptide selected from the group consisting of albumin and protamine.

10. A method according to claim 5, wherein said non-absorbable carrier moiety is a polyamine selected from the group consisting of spermine and spermidine.

11. A method according to claim 5, wherein said conjugate has the formula:

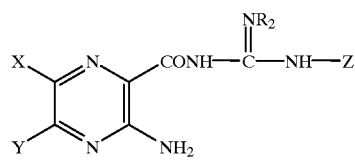

wherein:

X is selected from the group consisting of chloro, bromo, iodo, loweralkyl, lower-cycloalkyl having from 3 to 7 carbons, phenyl, chlorophenyl, bromophenyl, X'-thio and X'-sulfonyl wherein X' is selected from the group consisting of loweralkyl and phenyl-loweralkyl;

Y is selected from the group consisting of hydroxyl, mercapto, loweralkyloxy, loweralkylthio, chloro, lower alkyl, lowercycloalkyl having from 3 to 6 carbons, phenyl, amino having the structure:

wherein

R is selected from the group consisting of hydrogen, amino, amidino, lower-cycloalkyl having 3 to 6 carbon atoms, loweralkyl, hydroxyloweralkyl, halo-lower alkyl, lower-(cycloalkylalkyl) having 3 to 6 carbons in the ring, phenyl-loweralkyl, lower-(alkylaminoalkyl), lower-alkenyl, phenyl, halophenyl, and lower-alkylphenyl;

$R_1$ is selected from the group consisting of hydrogen, lower alkyl, loweralkenyl, and additionally;

R and $R_1$ can be joined to form a lower alkylene;

$R_2$ is selected from the group consisting of hydrogen and loweralkyl; and

Z is a non-absorbable carrier moiety covalently linked to the adjacent nitrogen atom;

or a pharmaceutically acceptable salt thereof.

12. A method according to claim 11, wherein X is chloro and Y is amino.

13. A method according to claim 11, wherein X is chloro and Y is chloro.

14. A method according to claim 11, wherein R, $R_1$, and $R_2$ are hydrogen.

15. A method according to claim 1, further comprising the step of topically applying a $P2Y_2$ receptor agonist to a mucosal surface of said subject in an amount effective to stimulate chloride secretion by said mucosal surface.

16. A pharmaceutical formulation, comprising:

a sodium channel blocker in a pharmaceutically acceptable carrier;

wherein said sodium channel blocker is a covalent conjugate of a pyrazinoylguanidine sodium channel blocker and a non-absorbable carrier moiety;

subject to the proviso that said non-absorbable carrier moiety is not bovine serum albumin or rabbit serum albumin.

17. A pharmaceutical formulation according to claim 16, said sodium channel blocker included in said composition in an amount effective to inhibit the reabsorption of water by mucosal surfaces.

18. A pharmaceutical formulation according to claim 16, said sodium channel blocker included in said composition in an amount effective to inhibit the reabsorption of water by mucosal surfaces.

19. A pharmaceutical formulation according to claim 16, wherein said non-absorbable carrier moiety is selected from the group consisting of carbohydrates, proteins, peptides, polyamines, and water soluble linear polymers.

20. A pharmaceutical formulation according to claim 16, wherein said non-absorbable carrier moiety is a water soluble linear polymer selected from the group consisting of polyvinylpyrrolidone, polyethylene glycol, nonylphenol ethoxylates, and polyvinyl alcohol.

21. A pharmaceutical formulation according to claim 16, wherein said non-absorbable carrier moiety is a carbohydrate selected from the group consisting of sugars and polysaccharides.

22. A pharmaceutical formulation according to claim 16, wherein said non-absorbable carrier moiety is a carbohydrate selected from the group consisting of dextran, lactose, sialic acid, and mannitol.

23. A pharmaceutical formulation according to claim 16, wherein said non-absorbable carrier moiety is a protein or peptide selected from the group consisting of albumin and protamine.

24. A pharmaceutical formulation according to claim 16, wherein said non-absorbable carrier moiety is a polyamine selected from the group consisting of spermine and spermidine.

25. A pharmaceutical formulation according to claim 16, wherein said conjugate has the formula:

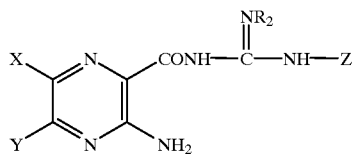

wherein:

X is selected from the group consisting of chloro, bromo, iodo, lower alkyl, lower-cycloalkyl having from 3 to 7 carbons, phenyl, chlorophenyl, bromophenyl, X'-thio and X'-sulfonyl wherein X' is selected from the group consisting of loweralkyl and phenyl-loweralkyl;

Y is selected from the group consisting of hydroxyl, mercapto, loweralkyloxy, loweralkylthio, chloro, lower alkyl, lowercycloalkyl having from 3 to 6 carbons, phenyl, amino having the structure:

wherein

R is selected from the group consisting of hydrogen, amino, amidino, lower-cycloalkyl having 3 to 6 carbon atoms, loweralkyl, hydroxyloweralkyl, halo-loweralkyl, lower-(cycloalkylalkyl) having 3 to 6 carbons in the ring, phenyl-loweralkyl, lower-(alkylaminoalkyl), lower-alkenyl, phenyl, halophenyl, and lower-alkylphenyl;

$R_1$ is selected from the group consisting of hydrogen, loweralkyl, loweralkenyl, and additionally;

R and $R_1$ can be joined to form a lower alkylene;

$R_2$ is selected from the group consisting of hydrogen and loweralkyl; and

Z is a non-absorbable carrier moiety covalently linked to the adjacent nitrogen atom;

or a pharmaceutically acceptable salt thereof.

26. A pharmaceutical formulation according to claim 25, wherein X is chloro and Y is chloro.

27. A pharmaceutical formulation according to claim 25, wherein X is chloro and Y is amino.

28. A pharmaceutical formulation according to claim 25, wherein R, R₁, and R₂ are hydrogen.

29. A pharmaceutical formulation according to claim 16, further comprising a P2Y₂ receptor agonist.

30. A pharmaceutical formulation according to claim 29, said P2Y₂ receptor agonist included in an amount effective to stimulate chloride secretion by airway surfaces.

31. A pharmaceutical formulation according to claim 29, said P2Y₂ receptor agonist included in an amount effective to stimulate chloride secretion and water secretion by airway surfaces.

32. A pharmaceutical formulation according to claim 16, wherein said carrier is an aqueous carrier solution.

33. A compound useful as a sodium channel blocker, said compound comprising a covalent conjugate of a pyrazinoylguanidine sodium channel blocker and a non-absorbable carrier moiety;

subject to the proviso that said non-absorbable carrier moiety is not bovine serum albumin, rabbit serum albumin or agarose.

34. A compound according to claim 33, wherein said non-absorbable carrier moiety is selected from the group consisting of carbohydrates, proteins, peptides, polyamines, and water soluble linear polymers.

35. A compound according to claim 33, wherein said non-absorbable carrier moiety is a water soluble linear polymer selected from the group consisting of polyvinylpyrrolidone, poyethylene glycol, nonylphenol ethoxylates, polyvinyl alcohol.

36. A compound according to claim 33, wherein said non-absorbable carrier moiety is a carbohydrate selected from the group consisting of sugars and polysaccharides.

37. A compound according to claim 33, wherein said non-absorbable carrier moiety is a carbohydrate selected from the group consisting of dextran, lactose, sialic acid and mannitol.

38. A compound according to claim 33, wherein said non-absorbable carrier moiety is a protein or peptide selected from the group consisting of albumin and protamine.

39. A compound according to claim 33, wherein said non-absorbable carrier moiety is a polyamine selected from the group consisting of spermine and spermidine.

40. A compound according to claim 33, wherein said conjugate has the formula:

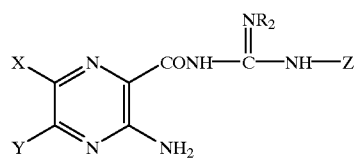

wherein:
X is selected from the group consisting of chloro, bromo, iodo, loweralkyl, lower-cycloalkyl having from 3 to 7 carbons, phenyl, chlorophenyl, bromophenyl, X'-thio and X'-sulfonyl wherein X' is selected from the group consisting of loweralkyl and phenyl-loweralkyl;

Y is selected from the group consisting of hydroxyl, mercapto, loweralkyloxy, lower alkylthio, chloro, loweralkyl, lowercycloalkyl having from 3 to 6 carbons, phenyl, amino having the structure:

wherein
R is selected from the group consisting of hydrogen, amino, amidino, lower-cycloalkyl having 3 to 6 carbon atoms, loweralkyl, hydroxyloweralkyl, haloloweralkyl, lower-(cycloalkylalkyl) having 3 to 6 carbons in the ring, phenyl-loweralkyl, lower-(alkylaminoalkyl), lower-alkenyl, phenyl, halophenyl, and lower-alkylphenyl;

R₁ is selected from the group consisting of hydrogen, loweralkyl, loweralkenyl, and additionally;

R and R₁ can be joined to form a loweralkylene;

R₂ is selected from the group consisting of hydrogen and loweralkyl; and

Z is a non-absorbable carrier moiety covalently linked to the adjacent nitrogen atom;

or a pharmaceutically acceptable salt thereof.

41. A compound according to claim 40, wherein X is chloro and Y is chloro.

42. A compound according to claim 40, wherein X is chloro and Y is amino.

43. A compound according to claim 40, wherein R, R₁, and R₂ are hydrogen.

* * * * *